(12) United States Patent
Oetken et al.

(10) Patent No.: US 11,609,322 B2
(45) Date of Patent: Mar. 21, 2023

(54) GROUND MATERIAL DENSITY MEASUREMENT SYSTEM

(71) Applicant: Caterpillar Paving Products Inc., Brooklyn Park, MN (US)

(72) Inventors: Nicholas A. Oetken, Brooklyn Park, MN (US); Tod A. Oblak, Pittsburgh, PA (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 565 days.

(21) Appl. No.: 16/678,443

(22) Filed: Nov. 8, 2019

(65) Prior Publication Data
US 2021/0141080 A1    May 13, 2021

(51) Int. Cl.
| | | |
|---|---|---|
| *G01S 13/88* | (2006.01) | |
| *G06T 7/62* | (2017.01) | |
| *G01N 33/24* | (2006.01) | |
| *G06T 7/514* | (2017.01) | |

(52) U.S. Cl.
CPC .......... *G01S 13/885* (2013.01); *G01N 33/246* (2013.01); *G06T 7/514* (2017.01); *G06T 7/62* (2017.01); *G06T 2207/10036* (2013.01); *G06T 2207/30181* (2013.01)

(58) Field of Classification Search
CPC ........ G01S 13/00; G01S 13/885; G01S 15/89; G01S 19/14; G01S 13/89
See application file for complete search history.

(56) References Cited

U.S. PATENT DOCUMENTS

| | | |
|---|---|---|
| 5,384,715 A | 1/1995 | Lytton |
| 5,952,561 A | 9/1999 | Jaselskis et al. |
| 8,152,410 B2 | 4/2012 | Roth |
| 9,618,496 B2 | 4/2017 | Troxler |
| 9,658,104 B2 | 5/2017 | Treado et al. |
| 9,903,077 B2 | 2/2018 | Rio |
| 2017/0115114 A1* | 4/2017 | Birken ............... G01B 11/2513 |
| 2017/0269729 A1* | 9/2017 | Chintalapoodi ..... G01N 27/223 |

(Continued)

FOREIGN PATENT DOCUMENTS

| | | | | |
|---|---|---|---|---|
| CN | 106989776 B | * | 5/2019 | ............. G01D 21/02 |
| CN | 109782274 A | | 5/2019 | |

OTHER PUBLICATIONS

Soren-Nils Haubrock, "Quantification of soil properties for analyzing surface processes using spectroscopy and laser scanning," Humboldt-Universitat zu Berlin—Geographisches Institut.

*Primary Examiner* — Ming Wu
(74) *Attorney, Agent, or Firm* — Harrity & Harrity, LLP (57) ABSTRACT

A ground material density measurement system is disclosed. The ground material density measurement system may receive a moisture measurement associated with an amount of moisture on a ground surface of a section of ground material. The ground material density measurement system may determine a GPR measurement associated with the section of ground material. The ground material density measurement system may process the GPR measurement based on the moisture measurement to account for the amount of moisture. The ground material density measurement system may provide density information associated with the section of ground material based on the processed GPR measurement.

20 Claims, 4 Drawing Sheets

(56) References Cited

U.S. PATENT DOCUMENTS

| | | |
|---|---|---|
| 2019/0094202 A1 | 3/2019 | Troxler |
| 2019/0268497 A1* | 8/2019 | Shikagawa .......... H04N 1/4076 |
| 2019/0316190 A1* | 10/2019 | Drmanac ............. C12Q 1/6827 |
| 2020/0256976 A1* | 8/2020 | Roberts ................... E01C 23/01 |

* cited by examiner

GROUND MATERIAL DENSITY MEASUREMENT SYSTEM

TECHNICAL FIELD

The present disclosure relates generally to ground material density detection and, for example, to ground penetrating radar for ground material density detection.

BACKGROUND

During a compaction operation, a machine may use a ground penetrating radar (GPR) device to detect and/or measure a void (e.g., a space that includes air or other type of gas) in ground material (e.g., asphalt, soil, etc.). In such cases, the GPR device uses radar signals to image a subsurface of the ground material. Further, the GPR device uses electromagnetic radiation in a microwave band (e.g., ultra high frequency (UHF), very high frequencies (VHF), and/or the like) of the radio spectrum and detects the reflected signals from subsurface ground material or structures. An absence of subsurface ground material and/or structures may correspond to one or more voids, and a measurement of the one or more voids can be used to determine a density of the ground material. Various environmental characteristics may affect an accuracy of detecting and/or measuring the one or more voids, thus potentially preventing the machine from compacting the ground material as desired.

One approach to measuring asphalt density is disclosed in U.S. Pat. No. 8,152,410 that issued to Roth on Apr. 10, 2012 ("the '410 patent"). In particular, the '410 patent discloses that the GPR may be used to determine a thickness and moisture content of asphalt pavement.

While the GPR of the '410 patent may determine moisture of asphalt pavement, the '410 patent does not describe use of a sensor to detect moisture on a surface of the asphalt to account for effects of the moisture on the surface of the asphalt.

The ground material density measurement system of the present disclosure solves one or more of the problems set forth above and/or other problems in the art.

SUMMARY

According to some implementations, a method may include receiving imaging data of a ground surface of a section of ground material that is captured by a spectral reflectance sensor; determining, based on the imaging data, a moisture measurement associated with an amount of moisture on the ground surface; receiving a ground penetrating radar (GPR) measurement associated with the section of ground material; determining a density measurement of the section of ground material based on the moisture measurement and the GPR measurement; and providing the density measurement to indicate a density of the section of ground material.

According to some implementations, a GPR device may include a memory, and a processor, communicatively coupled to the memory, configured to: receive a moisture measurement associated with an amount of moisture on a ground surface of a section of ground material; determine a GPR measurement associated with the section of ground material; process the GPR measurement based on the moisture measurement to account for the amount of moisture; and provide density information associated with the section of ground material based on the processed GPR measurement.

According to some implementations, a system may include a spectral reflectance sensor, a GPR device, and an electronic control module configured to: cause the spectral reflectance sensor to provide imaging data of a ground surface of a section of ground material; determine a moisture measurement associated with an amount of moisture on the ground surface that is represented in the imaging data; cause the GPR device to provide a GPR measurement associated with the section of ground material; process, based on receiving the GPR measurement, the GPR measurement and the moisture measurement to determine a density of the section of ground material; and perform an action associated with the density of the section of ground material.

DETAILED DESCRIPTION

Figure 1:
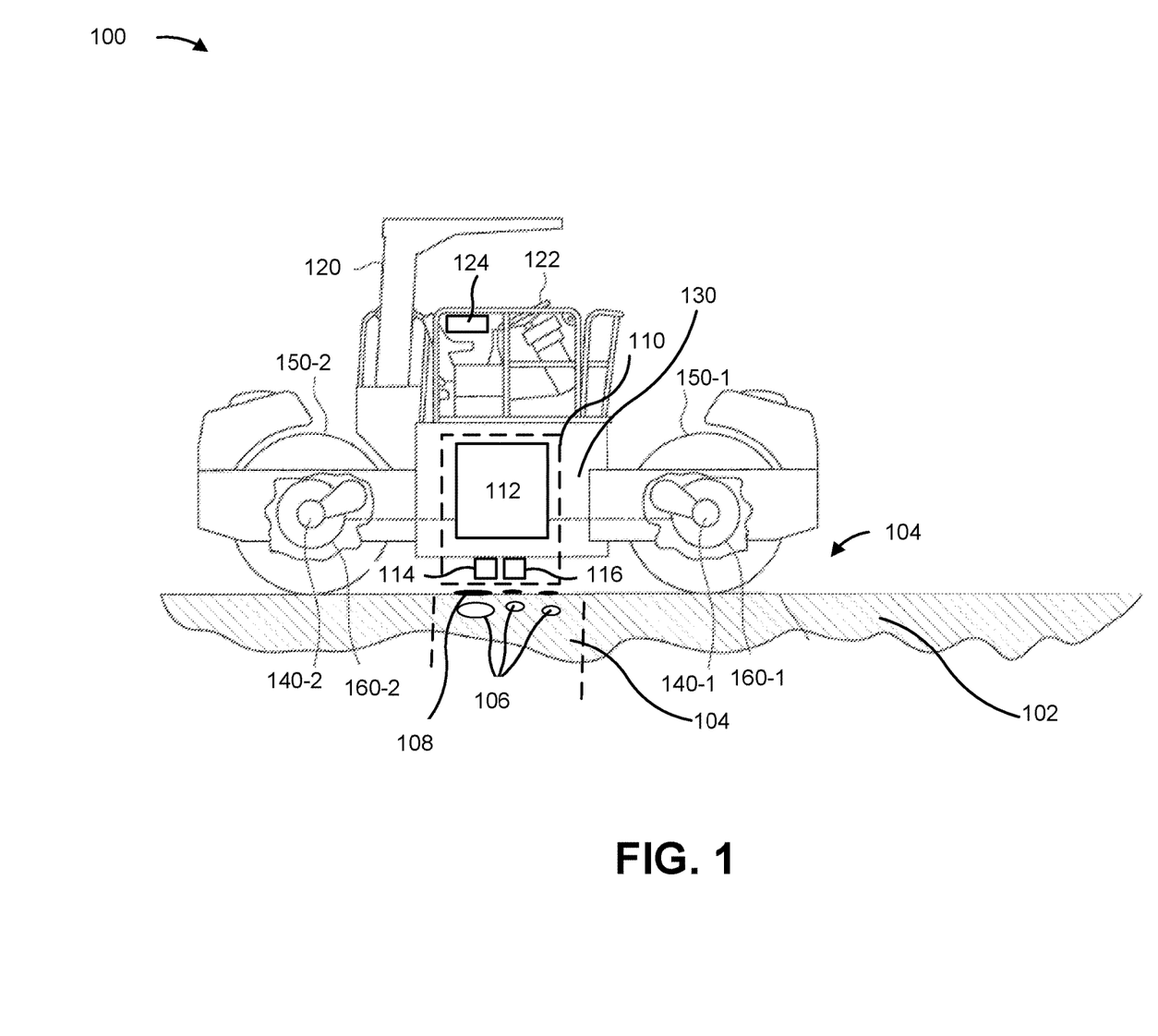
FIG. 1 is diagram of an example machine in which a ground material density measurement system may be implemented.

FIG. 1 is a diagram of an example compactor 100 described herein. The compactor 100 may refer to any type of machine for compacting a paving material, such as, for example, soil, sand, gravel, loose bedrock, asphalt, recycled concrete, bituminous mixtures, or any other compactable material. For example, the compactor 100 may include a rolling compactor, a plate compactor, a self-propelled compactor, a compactor towed behind a paving machine, or any other type of compaction device. While some implementations are described in connection with the compactor 100, other implementations may similarly apply to other machines, such as a machine that performs an operation associated with an industry such as, for example, mining, construction, farming, transportation, or any other industry.

In FIG. 1, the compactor 100 may be configured to compact ground material 102. As shown, the compactor 100 may be positioned over a section of ground material 104 that includes subsurface voids 106 and surface moisture 108. The compactor 100 may include a ground material density measurement system 110 that is to analyze the ground material 102, including the section of ground material 104, to determine a density of the ground material 102.

The subsurface voids 106 may be voids under the surface of the section of ground material 104 that correspond to volumes of air, fluid, moisture, and/or material that is not considered ground material 102. The subsurface voids 106 in the section of ground material 104 may cause the section of ground material 104 to be less dense than the remainder of the ground material 102 (which does not include subsurface voids 106).

As shown in FIG. 1, the ground material density measurement system 110 may include an electronic control module (ECM) 112, a ground penetrating radar (GPR) device 114, and a spectral reflectance sensor 116. As described herein, the GPR device 114 may be configured to detect and/or measure the subsurface voids 106 (e.g., determine dimensions of the subsurface voids 106), and the spectral reflectance sensor 116 may be configured to measure or detect the surface moisture 108 (e.g., and/or an amount of the surface moisture 108). The ECM 112 may receive respective measurements from the GPR device 114 and/or the spectral reflectance sensor 116 and determine the density of the section of ground material 104 based on the measurements. The section of ground material 104 may correspond to a location of the compactor 100 and/or may be defined by a positioning or orientation of the GPR device 114 and/or the spectral reflectance sensor 116. Accordingly, as the compactor 100, GPR device 114, and/or spectral reflectance sensor 116 traverse and/or scan the ground material 102, the section of ground material 104 may correspond to the position of the compactor 100, radar field of the GPR device 114, and/or field of view of the spectral reflectance sensor 116.

As shown, the compactor 100 may include an operator cab 120 with an operator interface that includes a steering wheel 122 or similar control device for controlling a travel direction of the compactor 100 and a display device 124 for presenting information associated with the compactor 100. The compactor 100 may further include an engine 130. The engine 130 may be configured to provide mechanical and/or electrical power to the compactor 100. For example, the engine 130 may be configured to provide power to components of the compactor 100, such as motors 140 (shown as "140-1" and "140-2") and other systems of the compactor 100 (e.g., the ground material density measurement system 110, hydraulics systems, brake systems, and/or the like). The motors 140 may be operably coupled to the engine 130 via electrical wires, fluid conduits, or any other suitable connection.

The compactor 100 may include various components to facilitate a compaction operation and/or prevent de-compaction or crushing of ground material 102 during the compaction operation. The compactor 100 may include one or more compacting elements, such as compacting drums 150 (shown as "150-1" and "150-2"). The compacting drums 150 may be rotatably mounted on the compactor 100. The compacting drums 150 may be operatively connected to the motors 140, such that a first motor 140-1 drives a first compacting drum 150-1 and a second motor 140-2 drives a second compacting drum 150-2. As shown, the compacting drums 150 may include and/or be controlled by vibratory mechanisms 160 (shown as "160-1" and "160-2"). The vibratory mechanisms 160 may include one or more variable vibratory mechanisms that may be controlled by ECM 112 to compact ground material 102, as described herein.

According to some implementations, the compactor 100 may include a location sensor to determine or indicate (e.g., via the display device 124) a location of the compactor 100, specifically, with respect to a work area. The location sensor may include one or more of a Global Positioning System (GPS), a Global Navigation Satellite System (GNSS), a laser-based positioning system, a trilateration/triangulation based system using one or more cellular or Wi-Fi networks, a pseudo-satellite, a ranging radio, a perception sensor, and/or the like. Additionally, or alternatively, the location sensor may be an external component configured to track movement of the compactor 100 using radar or similar tracking systems. The location sensor may be configured to generate location data indicative of the movement of the compactor 100.

As indicated above, FIG. 1 is provided as an example. Other examples may differ from what is described in connection with FIG. 1.

Figure 2:
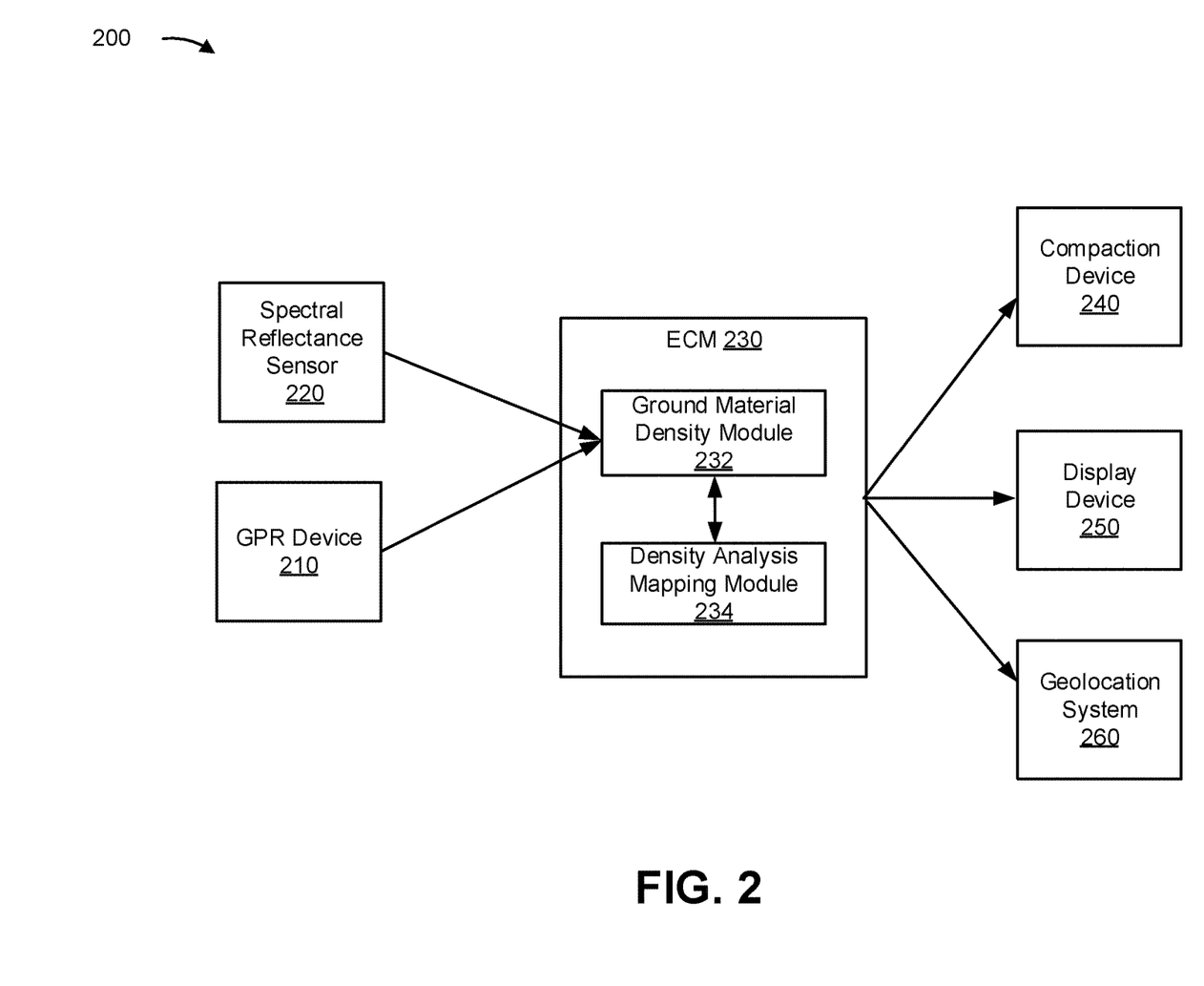
FIGS. 2 and 3 are diagrams of one or more example environments in which systems and/or methods described herein may be implemented.

FIG. 2 is a diagram of an example environment 200 in which systems and/or methods described herein may be implemented. As shown in FIG. 2, environment 200 may include a GPR device 210, a spectral reflectance sensor 220, an ECM 230 with a ground material density module 232 and a density analysis mapping module 234, a compaction device 240, a display device 250, and a geolocation system 260. Devices of environment 200 may interconnect via wired connections, wireless connections, or a combination of wired and wireless connections. As described herein, the GPR device 210, the spectral reflectance sensor 220, and/or the ECM 230 may be associated with a ground material density measurement system (e.g., the ground material density measurement system 110 of FIG. 1) that is configured to determine a density of ground material (e.g., the ground material 102 and/or section of ground material 104).

The GPR device 210 (which may correspond to the GPR device 114 of FIG. 1) may include one or more devices or components for transmitting, receiving, processing, and/or analyzing radio signals used to determine content of ground material. For example, the GPR device 210 may include a transmitter to emit a radar signal into the ground material, which is then reflected back to a receiver of the GPR device 210. The radar signal may have a frequency range between approximately 10 megahertz (MHz) and 2.6 gigahertz (GHz).

The GPR device 210 may be configured to adjust the frequency of the signals based on one or more characteristics of the ground material being analyzed. Such characteristics may include a type of the ground material (e.g., whether a particular soil type, solid rock, asphalt or pavement, concrete, and/or the like), a temperature of the ground material, an altitude of the ground material, and/or the like. For example, the GPR device 210 (e.g., via instructions from the ECM 230) may adjust parameters for transmitting the radar signal, receiving the radar signal, processing the radar signal, and/or analyzing the radar signal based on the characteristics. Accordingly, the GPR device 210 may be configured (or calibrated) to determine the content of the ground material. Correspondingly, the GPR device 210 may be configured to generate a GPR measurement of the content of the ground material. For example, the GPR device 210 may be configured to generate a density measurement of the ground material based on any voids (e.g., voids 106) detected in the ground material. Additionally, or alternatively, the GPR measurement may be provided as an image (e.g., generated by the GPR device 210 based on an analysis of the ground material).

A GPR measurement of the GPR device 210 may include a void measurement associated with a void within a subsurface of the section of ground material. For example, the GPR measurement may include a dimension of the void (e.g., a length, width, depth, volume, and/or the like) of a void in the ground material. Additionally, or alternatively, the GPR device 210 may include a material measurement corresponding to an amount of ground material within a section of the ground material. For example, the material measurement may include or be based on depth information associated with the ground material (e.g., corresponding to a distance from the surface of the ground material to another type of material beneath the ground material). For example, for asphalt, the depth information may include a depth (e.g., in meters, centimeters, and/or the like) from the surface to soil beneath the asphalt. Additionally, or alternatively, for a type of soil, the depth information may include a depth from the surface to bedrock beneath the soil.

The spectral reflectance sensor 220 (which may correspond to the spectral reflectance sensor 116 of FIG. 1) may include one or more devices or components for transmitting, receiving, processing, and/or analyzing reflectance of various wavelengths of light from the surface of the ground material. For example, the spectral reflectance sensor 220 may include a set (or array) of sensing elements (referred to herein as "pixels") that are configured to sense a measure of light (e.g., a particular spectrum of light) reflected from the surface of the ground material. The spectral reflectance sensor 220 may perform one or more scanning techniques (e.g., spatial scanning, spectral scanning, and/or the like) and/or scan processing techniques to generate an image (e.g., a 2D image) or model (e.g., a 3D model) according to the sensed light. Additionally, or alternatively, the spectral reflectance sensor 220 may include a single sensing element (or pixel) that is configured to sense light reflected from the ground material in a particular field of view. The field of view may be based on a position of the machine and/or or any suitable device (e.g., a lens or other type of optical element) capable of adjusting or defining the field of view. According to some implementations, the spectral reflectance sensor 220 may include and/or be associated with a light source (e.g., an emitter, such as a lamp) that is configured to enable or cause light to be reflected from the surface of the ground material.

The spectral reflectance sensor 220 may correspond to a hyperspectral sensor or other type of spectrometer that is capable of capturing images using various relatively narrow wavelength ranges (or spectral bands) of the electromagnetic spectrum. Similar to the GPR device 210, the spectral reflectance sensor 220 may be configured to detect moisture (e.g., droplets of a liquid or pools of a liquid) on a surface of the ground material based on one or more characteristics of the ground material. The spectral reflectance sensor 220 may be capable of determining and/or providing a moisture measurement corresponding to an amount of detected moisture on a surface of the ground material. According to some implementations, the spectral reflectance sensor 220 may include a camera or other type of imaging device that may be used to capture an image of the surface of the ground material to permit an image processing technique to be performed to identify and/or determine an amount of moisture on the surface (e.g., using object recognition, a computer vision technique, and/or the like).

The ECM 230, as described herein, may provide control of one or more systems of a machine (e.g., the compactor 100). In some implementations, the ECM 230 may determine a density of ground material (e.g., similar to the section of ground material 104) based on a GPR measurement from the GPR device 210 and/or imaging from the spectral reflectance sensor 220. According to the density of the ground material, the ECM 230 may control the compaction device 240, provide imaging associated with the density of the ground material to the display device 250, provide a density measurement to the display device 250 and/or the geolocation system 260, and/or the like.

The ECM 230 is implemented as a processor, such as a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component or controller. The processor is implemented in hardware, firmware, and/or a combination of hardware and software. The processor of the ECM 230 may be capable of being programmed to perform a function. In some implementations, one or more memories, including a random-access memory (RAM), a read only memory (ROM), and/or another type of dynamic or static storage device (e.g., a flash memory, a magnetic memory, and/or an optical memory) may store information and/or instructions for use by ECM 230. ECM 230 may include a memory (e.g., a non-transitory computer-readable medium) capable of storing instructions that, when executed, cause the processor to perform one or more processes and/or methods described herein.

The ECM 230 may execute the instructions to perform various control functions and processes to control the GPR device 210, the spectral reflectance sensor 220, and/or the compaction device 240, to alter a density of the ground material. For example, the ECM 230 may include any appropriate type of engine control system, component control system, and/or the like that is configured to iteratively perform one or more functions to cause a machine, such as the compactor 100 of FIG. 1, to be automatically positioned and/or operated (e.g., using one or more compaction components) to compact the ground material to a desired density. The ECM 230 may receive, from one or more other types of sensors, information associated with a physical environment of a ground material. For example, the ECM 230 may receive temperature measurements from a temperature sensor, pressure measurements from a pressure sensor, humidity measurements from a humidity sensor, and/or the like. In this way, the ECM 230 may be able to identify certain physical characteristics of a physical environment of the ground material.

The ECM 230 may use the ground material density module 232 to process measurements from the GPR device 210 and/or the spectral reflectance sensor 220 to determine a density of the ground material. For example, the ground material density module 232 may receive imaging from the spectral reflectance sensor 220 to determine whether there is any surface moisture on the ground material and one or more GPR measurements to determine whether there are any voids under the surface of the ground material (referred to herein as "subsurface ground material"). Based on the presence or amount of the surface moisture and/or dimensions of the voids, the ground material density module 232 is configured to determine the density of the ground. As described herein, the ground material density module 232 may use the density analysis mapping module 234 to analyze the measurements from the GPR device 210 and/or the spectral reflectance sensor 220.

To determine an amount of moisture on the surface of the ground, the ground material density module 232 may process the imaging data to identify any pixels of the imaging data that individually have a value that indicates the presence of water. For example, a set of pixels of an image may indicate the presence of a liquid (e.g., water, oil, tar, fuel, or any other type of liquid) on the surface of the ground material when the set of pixels has a value in a particular range. Accordingly, an amount of moisture may correspond to the quantity of pixels in the set of pixels that indicate the presence of water (e.g., a total number of pixels, a percentage of the pixels in the image data, and/or the like). Additionally, or alternatively, the amount of moisture may correspond to the values of the pixels. In such a case, an analysis of the spectral reflectance values at multiple particular wavelengths of the pixels may correspond to or utilize a scale that is representative of the amount of the liquid (e.g., a density, a volume, and/or the like). According to some implementations, the ground material density module 232 may determine the moisture measurement (e.g., corresponding to an amount of the moisture) based on a type of the ground material (e.g., the type of ground surface and/or the type of subsurface ground material).

The ground material density module 232 may determine a density of the ground material by adjusting a void measurement of the GPR device 210 based on an amount of moisture determined from the imaging data of the spectral reflectance sensor 220. For example, the ground material density module 232 may refer to a mapping of density analysis mapping module 234 to determine a degree of an adjustment to a dimension of a void measurement of the GPR device 210 according to the determined amount of moisture from the spectral reflectance sensor 220 imaging data. In such cases, the more moisture that is determined, the greater the adjustment to the void measurement (e.g., to increase or decrease the dimension of the void measurement). The ground material density module 232 may correspondingly adjust any subsurface imaging data generated by the GPR device 210 (e.g., to more accurately portray the content of the ground material and/or the size of a void in the ground material). Accordingly, the ground material density module 232 may generate density information (e.g., including imaging data of the ground material, a density measurement determined from a void measurement and/or amount of moisture, and/or the like) and enable the ECM 230 to use the density information to perform an action. For example, the ECM 230 may provide the density information to the compaction device 240 to cause the compaction device 240 to perform an operation (e.g., compact the ground material) according to the density information, provide the density information to the display device 250 to permit an operator to view the density information, and/or provide the density information to a geolocation system 260 that may store and/or use the density information to indicate the density information of ground material in an area (e.g., a work site) of the ground material.

The density analysis mapping module 234 may be any suitable data structure (e.g., a database, a table, an index, a graph, and/or the like) that may store one or more mappings of measurement values associated with GPR measurements of the GPR device 210 and/or moisture measurements associated with the spectral reflectance sensor 220. The density analysis mapping module 234 may include a plurality of tables, mappings, and/or the like that correspond to a variety of measurements associated with GPR device 210 and/or spectral reflectance sensor 220. For example, a data structure of density analysis mapping module 234 may include a mapping of GPR measurements (e.g., radar signal measurements) associated with the GPR device 210 to one or more subsurface measurements, such as ground density measurements, void measurements, depth measurements, and/or the like. Additionally, or alternatively, a data structure of density analysis mapping module 234 may include a mapping of spectral measurements (e.g., values of pixels) sensed by the spectral reflectance sensor 220 to moisture measurements associated with a presence of moisture and/or an amount of moisture (e.g., a volume of liquid, a density of liquid, and/or the like). In this way, the ECM 230 may be configured to process GPR measurements to determine subsurface measurements and/or spectral measurements to determine surface moisture measurements.

The ground material density module 232 may obtain and/or use the measurement values in density analysis mapping module 234 to determine a density of the ground material and/or account for moisture on the surface of the ground material (e.g., similar to surface moisture 108) according to a model. For example, the model may combine the GPR measurements and/or the spectral measurements to output a density according to any suitable technique. In some implementations, the ground material density module 232 may process the GPR measurements and a determined moisture measurement.

Furthermore, depending on the environmental characteristics of a machine associated with ECM 230 (e.g., as determined by one or more sensors of the machine, temperature sensors, pressure sensors, position sensors, and/or the like), the ground material density module 232 may use different mappings of the density analysis mapping module 234 to determine a density of the ground material. For example, one or more mappings may be configured according to certain characteristics of the ground material described herein. In this way, the ground material density module 232 may use one set of mappings to determine a density of asphalt and another set of mappings to determine a density of soil. Additionally, or alternatively, the ground material density module 232 may use one set of mappings for relatively cool ground material (e.g., asphalt that is ambient temperature, such as relatively old asphalt) and another set of mappings for a relatively hot ground material (e.g., freshly laid or relatively new asphalt). Accordingly, the ECM 230 may use adjustment values in the density analysis mapping module 234 to adjust and/or determine density information of ground material.

Figure 3:
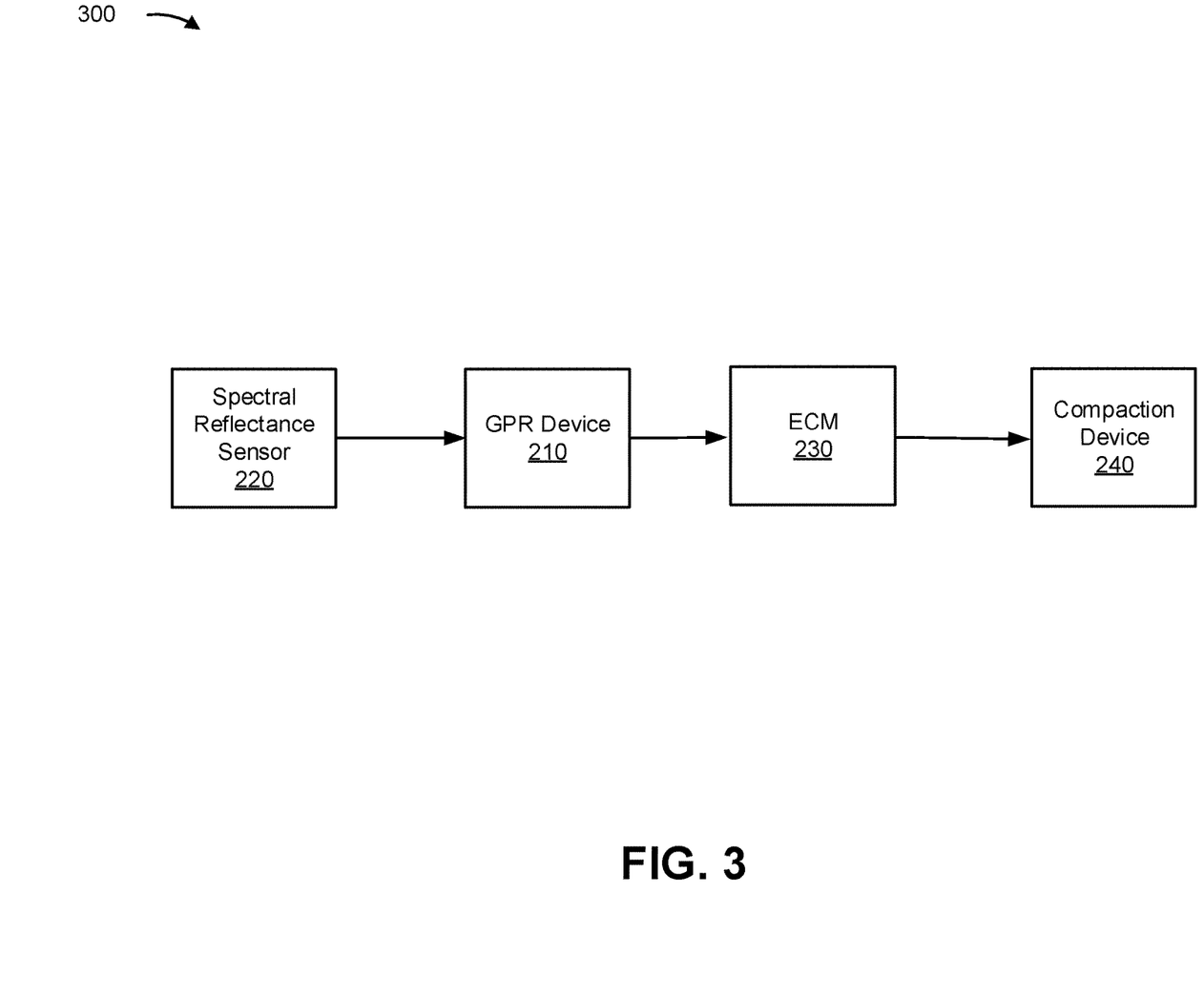

FIG. 3 is a diagram of another example environment 300 in which systems and/or methods described herein may be implemented. Similar to environment 200, the example environment 300 of FIG. 3, includes the GPR device 210, the spectral reflectance sensor 220, the ECM 230, and the compaction device 240. In example implementation 300, the GPR device 210 is configured to adjust a GPR measurement according to information from the spectral reflectance sensor 220 to determine the density of ground material. For example, the GPR device 210 may include one or more modules, similar to the ground material density module 232 and the density analysis mapping module 234 of the ECM 230, to determine and provide density information to the ECM 230 to enable control of the compaction device 240.

In FIG. 3, the GPR device 210 may be configured to receive imaging data from the spectral reflectance sensor 220 and/or determine an amount of moisture on a surface of ground material (e.g., in a similar manner as described above). The GPR device 210 may include any suitable data structure that stores measurement adjustment values associated with GPR measurements of the GPR device 210 and/or moisture measurements associated with the spectral reflectance sensor 220. Accordingly, the GPR device 210 may adjust a GPR measurement based on imaging data and/or a moisture measurement received from the spectral reflectance sensor 220 to determine the density of the ground material.

The GPR device 210 is configured to enable the ECM 230 to continue to operate as previously designed by performing the one or more operations described herein to determine a density of the ground material based on the GPR measurements and an amount of determined moisture on the surface of the ground material by the GPR device 210 and/or the spectral reflectance sensor 220.

The number and arrangement of devices shown in FIGS. 2 and 3 are provided as examples. In practice, there may be additional devices, fewer devices, different devices, or differently arranged than those shown in FIGS. 2 and 3. Furthermore, two or more devices shown in FIGS. 2 and 3 may be implemented within a single device, or a single device shown in FIGS. 2 and 3 may be implemented as multiple, distributed devices. Additionally, or alternatively, a set of devices (e.g., one or more devices) in FIGS. 2 and 3 may perform one or more functions described as being performed by another set of devices in FIGS. 2 and 3.

Figure 4:
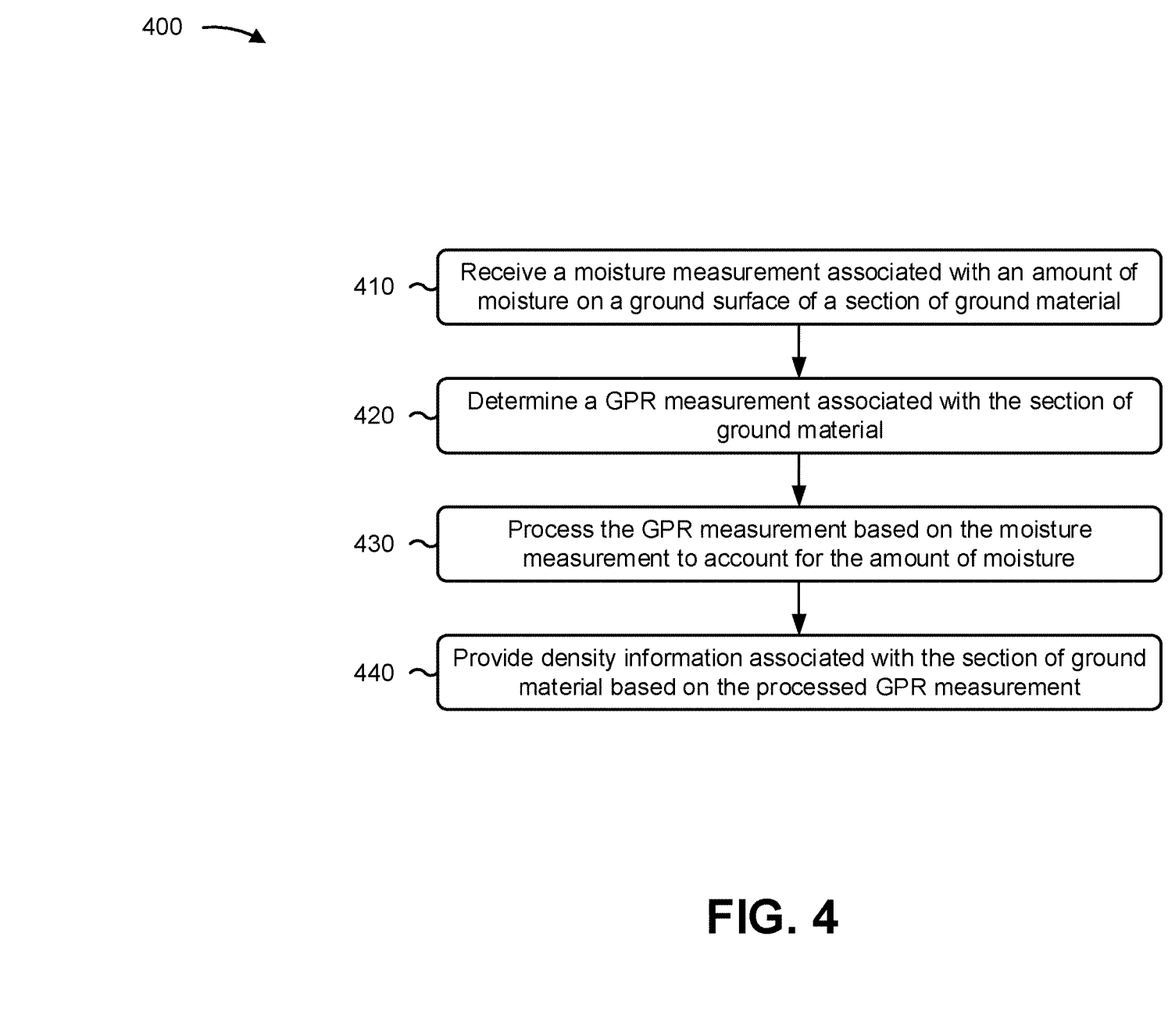
FIG. 4 is a flowchart of an example process associated with ground material density measurement system described herein.

FIG. 4 is a flowchart of an example process 400 associated with a ground material density measurement system. In some implementations, one or more process blocks of FIG. 4 may be performed by the ground material density measurement system 110. In some implementations, one or more process blocks of FIG. 4 may be performed by another device or a group of devices separate from or including the ground material density measurement system 110, such as the GPR device 210, the spectral reflectance sensor 220, the ECM 230, and/or the like.

As shown in FIG. 4, process 400 may include receiving a moisture measurement associated with an amount of moisture on a ground surface of a section of ground material (block 410). For example, the ground material density measurement system 110 (e.g., using a processor, a memory, the ground material density module 232, the density analysis mapping module 234, and/or the like) may receive a moisture measurement associated with an amount of moisture on a ground surface of a section of ground material, as described above.

The ground material density measurement system 110 may receive imaging data of the ground surface of the section of ground material (e.g., imaging data that is captured by a spectral reflectance sensor) and determine, based on the imaging data, the moisture measurement associated with an amount of moisture on the ground surface. For example, the ground material density measurement system 110 may process the imaging data to identify individual values of a set of pixels of the imaging data that correspond to an amount of a liquid on the ground surface and determine the moisture measurement based on the individual values of the set of pixels. The imaging data and/or the moisture measurement may be received from a hyperspectral sensor configured to detect, measure, and/or provide the moisture measurement to indicate the amount of moisture on a ground surface.

The ground material density measurement system 110 may determine the moisture measurement by processing the imaging data to identify a set of pixels of the imaging data that individually have a value that is representative of a presence of a liquid on the ground surface, and determining the moisture measurement based on a quantity of the set of pixels and/or a percentage of the set of pixels. The moisture measurement may be determined based on individual values of the set of pixels, wherein the individual values are representative of an amount of the liquid on the ground surface. The moisture measurement may be determined based on a type of material on the ground surface or a type of material in the section of ground material.

As further shown in FIG. 4, process 400 may include determining a GPR measurement associated with the section of ground material (block 420). For example, the ground material density measurement system 110 (e.g., using a processor, a memory, the ground material density module 232, the density analysis mapping module 234, and/or the like) may determine a GPR measurement associated with the section of ground material, as described above.

The GPR measurement includes at least one of: a void measurement associated with a void within a subsurface of the section of ground material, or a material measurement associated with an amount of ground material within the section of ground material. The ground material density measurement system 110 may configure a spectral reflectance sensor to capture the imaging data based on the type of ground material and/or configure a GPR device to generate the GPR measurement based on the type of ground material. The spectral reflectance sensor and the GPR device may be mounted on a same machine and be configured to capture the imaging data and/or GPR measurement when the machine is positioned above the section of the ground material.

As further shown in FIG. 4, process 400 may include processing the GPR measurement based on the moisture measurement to account for the amount of moisture (block 430). For example, the ground material density measurement system 110 (e.g., using a processor, a memory, the ground material density module 232, the density analysis mapping module 234, and/or the like) may process the GPR measurement based on the moisture measurement to account for the amount of moisture, as described above.

The ground material density measurement system may adjust a void measurement associated with the GPR measurement based on the moisture measurement. The void measurement may be associated with a void within a subsurface of the section of ground material. The ground material density measurement system may determine the density of the section of ground material based on the adjusted void measurement.

The ground material density measurement system may adjust subsurface imaging data of the section of ground material that is generated from a radar signal reflected from the section of ground material. The subsurface imaging data may be adjusted based on the moisture measurement.

As further shown in FIG. 4, process 400 may include providing density information associated with the section of ground material based on the processed GPR measurement (block 440). For example, the ground material density measurement system 110 (e.g., using a processor, a memory, the ground material density module 232, the density analysis mapping module 234, and/or the like) may provide density information associated with the section of ground material based on the processed GPR measurement, as described above.

The ground material density measurement system 110 may cause density information or an image of a subsurface of the section of ground material to be presented on a display, store the density information in association with a geographical map of an area including the section of ground material, and/or control a machine to alter the density of the section of ground material. The density information may include imaging data of the section of ground material and/or or a density measurement of the section of ground material. The density information may be provided to a display of a user interface, an ECM, a geolocation system configured to map densities of multiple sections of ground material at a work site, and/or the like. The section of ground material may correspond to a section of asphalt, and the density measurement is provided to an electronic control module of a compactor configured to compact the section of asphalt.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

INDUSTRIAL APPLICABILITY

A ground penetrating radar (GPR) measurement of a GPR device can be useful in determining a density of ground material. However, in previous techniques, when a GPR device is used to determine a density of ground material with surface moisture, GPR measurements from the GPR device may not accurately reflect an actual density of the ground material because the surface moisture can cause inaccuracies to exist in the GPR measurements (e.g., due to radio signals being distorted by the surface moisture). Accordingly, previous techniques for determining a density of ground material using a GPR device may cause a device (e.g., the electronic control module (ECM) 230) or a machine (e.g., the compactor 100) to inaccurately determine a density of the ground material, and/or correspondingly, to perform an action based on an inaccurate measurement of the density of the ground material. For example, under previous techniques, if the GPR device indicates an inaccurate density of asphalt for a paved surface, a compactor may not accurately compact the asphalt, and the useful life of the paved surface may be reduced (e.g., because the asphalt would be more susceptible to cracking under stress).

Some implementations described herein provide a ground material density measurement system (e.g., ground material density measurement system 110) that determines a ground material density based on a GPR measurement and surface moisture measurement associated with a determined amount of moisture on the surface of the ground material. The ground material density measurement system may use a hyperspectral sensor to accurately determine an amount moisture on the surface of a section of ground material and adjust a GPR measurement (e.g., adjust one or more dimensions of a void indicated in the GPR measurement) to account for the presence of the surface moisture.

In this way, the ground material density measurement system can provide a density measurement and/or corresponding density information that is more accurate than previous techniques. Accordingly, based on the improved accuracy, the ground material density measurement system conserves ground material resources (e.g., by improving useful life of compacted asphalt, gravel, and/or the like) for paving surfaces, hardware resources (e.g., by reducing component stress or damage caused by inaccurate or undesirable ground material compaction), consumable resources (e.g., by reducing operations to repair inaccurate or undesirable ground material compaction), and/or the like.

What is claimed is:

1. A method, comprising:
receiving, by a processor, imaging data of a ground surface of a section of ground material that is captured by a spectral reflectance sensor;
determining, by the processor and based on the imaging data, a moisture measurement associated with an amount of moisture on the ground surface;
receiving, by the processor, a ground penetrating radar (GPR) measurement that is determined by a GPR device,
wherein the GPR measurement is associated with the section of ground material, and
wherein the GPR device is different from the spectral reflectance sensor;
adjusting, by the processor and based on the moisture measurement, the GPR measurement;
determining, by the processor and based on adjusting the GPR measurement, a density measurement of the section of ground material; and
providing, by the processor, the density measurement to indicate a density of the section of ground material.

2. The method of claim 1, wherein the spectral reflectance sensor is a hyperspectral sensor configured to detect water on a surface that includes a characteristic of the section of ground material.

3. The method of claim 1, wherein determining the moisture measurement comprises:
processing the imaging data to identify a set of pixels of the imaging data that individually has a value that is representative of a presence of a liquid on the ground surface, and determining the moisture measurement based on at least one of:
a quantity of the set of pixels, or
a percentage of the set of pixels.

4. The method of claim 3, wherein the moisture measurement is determined based on individual values of the set of pixels,
wherein the individual values are representative of an amount of the liquid on the ground surface.

5. The method of claim 1, wherein the moisture measurement is determined based on a type of material on the ground surface or a type of material in the section of ground material.

6. The method of claim 1, wherein the GPR measurement includes a void measurement associated with a void within a subsurface of the section of ground material.

7. The method of claim 1, wherein the section of ground material corresponds to a section of asphalt and the density measurement is provided to an electronic control module of a compactor configured to compact the section of asphalt.

8. A ground penetrating radar (GPR) device, comprising:
a memory; and
a processor, communicatively coupled to the memory, configured to:
receive, from a spectral reflectance sensor, a moisture measurement associated with an amount of moisture on a ground surface of a section of ground material,
wherein the spectral reflectance sensor is different from the GPR device;
determine a GPR measurement associated with the section of ground material;
adjust the GPR measurement based on the moisture measurement to account for the amount of moisture; and
provide density information associated with the section of ground material based on adjusting the GPR measurement.

9. The GPR device of claim 8, wherein the spectral reflectance sensor is a hyperspectral sensor configured to detect and provide the moisture measurement to indicate the amount of moisture on the ground surface.

10. The GPR device of claim 8, wherein the GPR measurement includes at least one of:
a void measurement associated with a void within a subsurface of the section of ground material, or
a material measurement associated with an amount of ground material within the section of ground material.

11. The GPR device of claim 8, wherein the processor, when adjusting the GPR measurement, is configured to:
adjust a void measurement associated with the GPR measurement based on the moisture measurement,
wherein the void measurement is associated with a void within a subsurface of the section of ground material; and
determine the density of the section of ground material based on adjusting the void measurement.

12. The GPR device of claim 8, wherein the processor, when adjusting the GPR measurement, is configured to:
adjust subsurface imaging data of the section of ground material that is generated from a radar signal reflected from the section of ground material, wherein the subsurface imaging data is adjusted based on the moisture measurement.

13. The GPR device of claim 8, wherein the density information includes at least one of:
   imaging data of the section of ground material, or
   a density measurement of the section of ground material.

14. The GPR device of claim 8, wherein the density information is provided to at least one of:
   a display of a user interface,
   an electronic control module, or
   a geolocation system configured to map densities of multiple sections of ground material at a work site.

15. A system may include:
   a spectral reflectance sensor;
   a ground penetrating radar (GPR) device,
      wherein the GPR device is different from the spectral reflectance sensor; and an electronic control module configured to:
      cause the spectral reflectance sensor to provide imaging data of a ground surface of a section of ground material;
      determine a moisture measurement associated with an amount of moisture on the ground surface that is represented in the imaging data;
      cause the GPR device to provide a GPR measurement associated with the section of ground material;
      adjust, based on the moisture measurement, the GPR measurement;
      determine, based on adjusting the GPR measurement, a density of the section of ground material; and
      perform an action associated with the density of the section of ground material.

16. The system of claim 15, wherein the electronic control module is configured to determine a type of ground material associated with the section of ground material,
   wherein the electronic control module is configured to at least one of:
      configure the spectral reflectance sensor to capture the imaging data based on the type of ground material, or
      configure the GPR device to generate the GPR measurement based on the type of ground material.

17. The system of claim 15, wherein the spectral reflectance sensor and the GPR device are mounted on a same machine as the electronic control module,
   wherein the electronic control module is configured to cause the spectral reflectance sensor to capture the imaging data and the GPR device to generate the GPR measurement when the machine is positioned above the section of the ground material.

18. The system of claim 15, wherein the electronic control module is configured to:
   process the imaging data to identify individual values of a set of pixels of the imaging data that correspond to an amount of a liquid on the ground surface; and
   determine the moisture measurement based on the individual values of the set of pixels.

19. The system of claim 15, wherein the electronic control module, when adjusting the GPR measurement, is to:
   identify, from the GPR measurement, a void in the section of ground material based on a void measurement that includes dimensions of the void; and
   adjust the dimensions of the void based on the moisture measurement.

20. The system of claim 15, wherein the electronic control module, when performing the action, is to at least one of:
   cause density information or an image of a subsurface of the section of ground material to be presented on a display;
   store the density information in association with a geographical map of an area including the section of ground material; or
   control a machine to alter the density of the section of ground material.

* * * * *